US010610623B2

(12) United States Patent
Robinson et al.

(10) Patent No.: US 10,610,623 B2
(45) Date of Patent: Apr. 7, 2020

(54) SYSTEMS AND METHODS FOR INCREASING ABSORBENT CAPACITY OF A DRESSING

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 578 days.

(21) Appl. No.: 14/619,743

(22) Filed: Feb. 11, 2015

(65) Prior Publication Data
US 2015/0231314 A1 Aug. 20, 2015

Related U.S. Application Data

(60) Provisional application No. 61/939,958, filed on Feb. 14, 2014.

(51) Int. Cl.
*A61M 1/00* (2006.01)
*A61F 13/00* (2006.01)
*A61F 13/02* (2006.01)

(52) U.S. Cl.
CPC ..... *A61M 1/0088* (2013.01); *A61F 13/00017* (2013.01); *A61F 13/00042* (2013.01);
(Continued)

(58) Field of Classification Search
CPC ......... A61M 1/0088; A61M 2205/3331; A61F 13/00017; A61F 13/00042; A61F 13/00068
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 755496 2/2002
(Continued)

OTHER PUBLICATIONS

Malin Malmsjo et al, The Effects of Variable, Intermittent, and Continuous Negative Pressure Wound Therapy, Using Foam or Gauze, on Wound Contraction, Granulation Tissue Formation, and Ingrowth Into the Wound Filler, Jan. 24, 2012, Eplasty, 12:5, 42-54.*
(Continued)

*Primary Examiner* — Adam Marcetich
*Assistant Examiner* — Jessica R Arble

(57) ABSTRACT

Systems and methods for managing fluid absorption from a tissue site are described. A dressing having an absorbent is positioned proximate the tissue site to receive fluid from the tissue site. A reduced-pressure source is fluidly coupled to the dressing and supplies reduced pressure to the dressing. The reduced pressure is periodically decreased to distribute fluid in the absorbent and managed fluid absorption. The system includes a reduced-pressure source and a container having an upstream layer, a downstream layer, and an absorbent between the upstream layer and the downstream layer. The system also includes a sealing member for forming a therapeutic environment having the container and a controller configured to operate the reduced pressure source to intermittently supply reduced pressure to the therapeutic environment and periodically decrease the reduced pressure in the therapeutic environment.

15 Claims, 5 Drawing Sheets

(52) U.S. Cl.
CPC .... *A61F 13/00068* (2013.01); *A61F 13/0209* (2013.01); *A61F 13/0216* (2013.01); *A61M 1/0037* (2013.01); *A61M 1/0096* (2014.02); *A61M 2205/3331* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,198,046 B1* | 4/2007 | Argenta | A61M 1/0088 128/897 |
| 2002/0013560 A1* | 1/2002 | Erspamer | A61F 13/15203 604/381 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2008/0009812 A1* | 1/2008 | Riesinger | A61F 13/00012 604/305 |
| 2008/0208147 A1* | 8/2008 | Argenta | A61M 1/0037 604/290 |
| 2009/0227969 A1* | 9/2009 | Jaeb | A61M 1/0088 604/313 |
| 2009/0299303 A1* | 12/2009 | Seegert | A61M 1/0088 604/290 |
| 2010/0042074 A1* | 2/2010 | Weston | A61M 1/0066 604/543 |
| 2010/0305490 A1 | 12/2010 | Coulthard et al. | |
| 2011/0004172 A1* | 1/2011 | Eckstein | A61F 13/00068 604/313 |
| 2011/0077605 A1* | 3/2011 | Karpowicz | A61M 1/0001 604/318 |
| 2014/0163486 A1* | 6/2014 | Riesinger | A61M 1/0088 604/304 |

FOREIGN PATENT DOCUMENTS

| | | |
|---|---|---|
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |

(56) References Cited

FOREIGN PATENT DOCUMENTS

| WO | 94/20041 A1 | 9/1994 |
|---|---|---|
| WO | 96/05873 A1 | 2/1996 |
| WO | 97/18007 A1 | 5/1997 |
| WO | 99/13793 A1 | 3/1999 |
| WO | 2012141999 A1 | 10/2012 |

OTHER PUBLICATIONS

International Search Report and Written Opinion for PCT/US2015/015497 dated May 7, 2015.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukic, Ž. Maksimovic, Đ. Radak, and P. Peška, "Vacuum Therapy in the Treatment of Peripheral Blood Vessels," Timok Medical Journal 11 (1986), pp. 161-164 (copy and certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C.® Therapy Clinical Guidelines: A Reference Source for Clinicians (Jul. 2007).

\* cited by examiner

SYSTEMS AND METHODS FOR INCREASING ABSORBENT CAPACITY OF A DRESSING

CROSS-REFERENCE TO RELATED APPLICATIONS

This application claims priority to and the benefit of U.S. Provisional Patent Application No. 61/939,958, filed Feb. 14, 2014, entitled "SYSTEMS AND METHODS FOR INCREASING ABSORBENT CAPACITY OF A DRESSING," to Timothy Mark Robinson, and Christopher Brian Locke, which is hereby incorporated by reference.

FIELD

The present disclosure relates generally to absorbent dressings, and more particularly, but without limitation, to a method for increasing an absorbent capacity of a dressing.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and microdeformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

According to an illustrative, non-limiting embodiment, a method for managing fluid absorption from a tissue site is described. A dressing having an absorbent may be positioned proximate the tissue site to receive fluid from the tissue site. A reduced-pressure source may be fluidly coupled to the dressing and supply reduced pressure to the dressing. The reduced pressure may be periodically decreased to distribute fluid in the absorbent.

According to another illustrative embodiment, a method for increasing the fluid capacity of an absorbent is described. A manifold may be positioned adjacent a tissue site, and the absorbent may be positioned proximate the manifold. A drape may be placed over the absorbent and the manifold. A reduced-pressure source may be fluidly coupled to the manifold and may supply reduced pressure to the tissue site. The reduced pressure may be periodically decreased.

According to another illustrative embodiment, a system for providing reduced pressure to a tissue site is described. The system may include a reduced-pressure source and a container configured to be positioned between the tissue site and the reduced-pressure source. The container may include an upstream layer formed from non-woven material, a downstream layer, and an absorbent formed from a super-absorbent polymer disposed between the upstream layer and the downstream layer. The system may also include a sealing member configured to be sealed over the container to form a therapeutic environment. The system may further include a controller configured to operate the reduced pressure source to intermittently supply reduced pressure to the therapeutic environment and periodically decrease the reduced pressure in the therapeutic environment.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached drawings, which are incorporated by reference herein, and wherein.

DETAILED DESCRIPTION

New and useful systems, methods, and apparatuses associated with increasing a fluid capacity of an absorbent dressing in a reduced-pressure environment are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
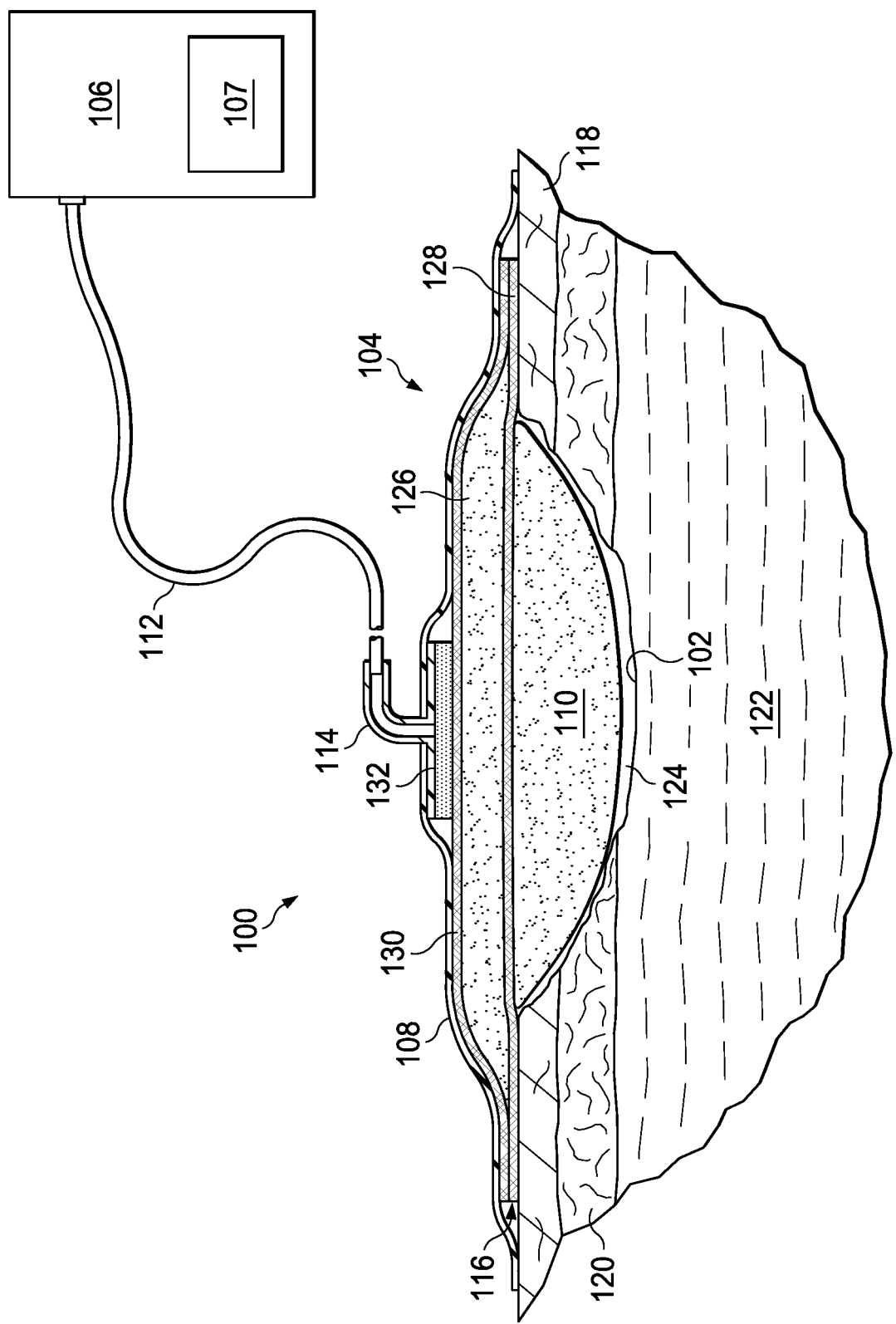
FIG. 1 is a partial sectional view of a system for providing reduced-pressure therapy to a tissue site in accordance with some embodiments.

FIG. 1 is a partial section of a reduced-pressure therapy system 100 illustrating details that may be associated with some embodiments. In some embodiments, the reduced-pressure therapy system 100 may include a dressing, such as a dressing 104, fluidly coupled to a reduced-pressure source, such as a reduced-pressure source 106 having a controller 107. In some embodiments, the reduced-pressure source 106 may be fluidly coupled to the dressing 104 by a conduit, such as a tube 112, and a connector, such as a connector 114. In some embodiments, a filter 132 may be disposed within a fluid channel of the connector 114. The dressing 104 may generally include a medical drape, such as a drape 108, an absorbent pouch, such as the container 116, and a tissue interface, such as a manifold 110. The drape 108 may be attached to an epidermis 118. In some embodiments, the drape 108 can substantially prevent the leakage of fluids while allowing vapor to egress through the drape 108. In some embodiments, the dressing 104 having the container 116 may be collectively referred to as an absorbent dressing. In some embodiments, the container 116 may have an absorbent, such as an absorbent 126, a first outer layer, such as an upstream layer 128, and a second outer layer, such as a downstream layer 130.

In general, components of the reduced-pressure therapy system 100 may be coupled directly or indirectly to each other. For example, the reduced-pressure source 106 may be directly coupled to the connector 114 and indirectly coupled to the manifold 110 through the connector 114. Components may be fluidly coupled to each other to provide a path for transferring fluids (such as liquid and/or gas) between the components. In some embodiments, components may be fluidly coupled with a tube, such as the tube 112, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the manifold 110, may be placed within, over, on, against, or otherwise adjacent a tissue site. For example, the manifold 110 may be placed against the tissue site 102, and the drape 108 may be placed over the manifold 110 and sealed to tissue proximate the tissue site 102. Tissue proximate a tissue site is often undamaged epidermis peripheral to the tissue site. Thus, the drape 108 can provide a sealed therapeutic environment 124 proximate the tissue site 102. The sealed therapeutic environment 124 may be substantially isolated from the external environment, and the reduced-pressure source 106 can reduce the pressure in the sealed therapeutic environment 124. Reduced pressure applied across a tissue site through a tissue interface in a sealed therapeutic environment can induce macrostrain and microstrain in the tissue site, as well as remove exudates and other fluids from the tissue site. The removed exudates and other fluids can be collected in a container, such as the container 116, and disposed of properly.

The fluid mechanics of using a reduced-pressure source to reduce pressure in another component or location, such as within a sealed therapeutic environment 124, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, in the context of reduced-pressure therapy, the term "downstream" typically implies a position in a fluid path relatively closer to a reduced-pressure source, and conversely, the term "upstream" implies a position relatively further away from a reduced-pressure source. Similarly, it may be convenient to describe certain features in terms of fluid "inlet" or "outlet" in such a frame of reference. However, a fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location. In some illustrative embodiments, the tissue site 102 may be a wound that extends through the epidermis 118, through a dermis 120, and into subcutaneous tissue 122, as shown in FIG. 1.

"Reduced pressure" generally refers to a pressure less than a local ambient pressure, such as the ambient pressure in a local environment external to the sealed therapeutic environment 124 provided by the drape 108. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 106, may be a reservoir of air at a reduced pressure, or may be a manual or electrically-powered device that can reduce the pressure in a sealed volume, such as a vacuum pump, a suction pump, a wall-suction port available at many healthcare facilities, or a micro-pump, for example. In some embodiments, a micro-pump may be a pump configured to be coupled adjacent the drape 108. A reduced-pressure source may be housed within or used in conjunction with other components, such as sensors, processing units, alarm indicators, memory, databases, software, display devices, or operator interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa). Generally, a reduced-pressure source may be capable of reducing a pressure in a sealed therapeutic environment to a therapy pressure. A therapy pressure may be a reduced pressure at which a caregiver has determined optimal therapy may be provided. In some embodiments, a reduced-pressure source may use a therapy pressure as a target pressure for reduced-pressure therapy. For example, a reduced-pressure source may operate until a pressure in a sealed therapeutic environment is approximately the therapy pressure. If a pressure in a sealed therapeutic environment varies from a therapy pressure, the reduced-pressure source may operate to lower the pressure back to the therapy pressure.

A reduced pressure source may include a user interface. A user interface may be a device configured to allow communication between a controller and an environment external to a reduced-pressure source. In some embodiments, an external environment may include an operator or a computer system configured to interface with a reduced-pressure source, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with a reduced-pressure source. In some embodiments, a user interface may display information for an external environment such as a duration of therapy, a type of therapy, an amount of reduced pressure being supplied, an amount of instillation solution being provided, a fluid level of a container, or a fluid level of a cartridge, for example.

A reduced-pressure source may also include one or more pressure sensors. A pressure sensor, may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure.

A reduced-pressure source may include one or more moisture sensors. A moisture sensor may be a device configured to measure a relative humidity of a space. In some embodiments, a moisture sensor may also be referred to as a hygrometer. In some embodiments, a moisture sensor may be a capacitive humidity sensor configured to measure the effect of humidity on a dielectric constant of a polymer or metal oxide material. In other embodiments, a moisture sensor may be a resistive humidity sensor that is configured to measure an electrical resistance of a material as it changes in response to humidity. In other embodiments, other types of moisture sensors may be included in a reduced-pressure source.

A reduced-pressure source may include one or more valves. Generally, a valve may be configured to selectively permit fluid flow through the valve. A valve may be a ball valve, a gate valve, a butterfly valve, or other valve type that may be operated to control fluid flow through the valve. Generally, a valve may include a valve body having a flow passage, a valve member disposed in the flow passage and operable to selectively block the flow passage, and an actuator configured to operate the valve member. An actuator may be configured to position the valve member in a closed position, preventing fluid flow through the flow passage of the valve; an open position, permitting fluid flow through the fluid passage of the valve; or a metering position, permitting fluid flow through the flow passage of the valve at a selected flow rate. In some embodiments, the actuator may be a mechanical actuator configured to be operated by an operator. In some embodiments, the actuator may be an electromechanical actuator configured to be operated in response to the receipt of a signal input. For example, the actuator may include an electrical motor configured to receive a signal from a controller. In response to the signal, the electrical motor of the actuator may move the valve member of the valve. In some embodiments, a valve may be configured to selectively permit fluid communication between the reduced-pressure source 106 and the dressing 104. In some embodiments, the reduced-pressure source 106 may includes valves configured to permit venting of the dressing 104 by allowing ambient air to flow through the reduced-pressure source 106 to the dressing 104.

A reduced-pressure source may also include one or more flow meters. A flow meter may be a device configured to determine a fluid flow rate. A flow meter may include a mechanical flow meter, a pressure based flow meter, an optical flow meter, an open channel flow meter, a thermal mass flow meter, a vortex flow meter, electromagnetic, ultrasonic and coriolis flow meters, or a laser doppler flow meter, for example. A flow meter may determine a rate of fluid flow through a valve and transmit a signal to a controller corresponding to the determined flow rate.

A reduced-pressure source may include one or more controllers, such as the controller 107, communicatively coupled to components of the reduced-pressure source, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller: operating the valve; placing the valve in an open position, a closed position, or a metering position; and opening the valve, closing the valve, or metering the valve.

A controller may be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

A reduced-pressure source may also include a power source. A power source may be a device that supplies electric power to an electric load. A power source may include a battery, a direct current (DC) power supply, an alternating current (AC) power supply, a linear regulated power supply, or a switched-mode power supply, for example. A power supply may supply electric power to a controller, a sensor, a flow meter, a valve, a user interface, or a pump, for example.

A tissue interface, such as the manifold 110, can generally be adapted to contact a tissue site or other layers of a dressing, such as the drape 108. A tissue interface may be partially or fully in contact with a tissue site. If a tissue site is a wound, for example, a tissue interface may partially or completely fill the wound, or may be placed over the wound. A tissue interface may take many forms, and may be many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids from across a tissue site. A manifold may include flow channels or pathways that can distribute fluids provided to and removed from a tissue site. In one illustrative embodiment, the flow channels or pathways may be interconnected to improve distribution of fluids provided to or removed from a tissue site. For example, a manifold may be an open-cell foam, porous tissue collection, and other porous material such as gauze or felted mat that generally includes structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam material may be either hydrophobic or hydrophilic. In one non-limiting example, the manifold 110 may be reticulated polyurethane foam such as GranuFoam® dressing available from Kinetic Concepts, Inc. of San Antonio, Tex.

In some embodiments, such as embodiments in which the manifold 110 may be made from a hydrophilic material, the manifold 110 may also wick fluid away from a tissue site while continuing to distribute reduced pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within a sealed therapeutic environment 124 is reduced. For example, any or all of the surfaces of the manifold 110 may have an uneven, coarse, or jagged profile that can induce microstrains and stresses at a tissue site if reduced pressure is applied through the manifold 110.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two environments or components, such as between a therapeutic environment and a local external environment. A sealing member may be, for example, an impermeable or semi-permeable, elastomeric film or barrier that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery of, a portion of, or an entirety of a sealing member. Other example embodiments of an attachment device may include a double-sided tape, paste, hydrocolloid, hydrogel, silicone gel, organogel, or an acrylic adhesive.

A "container," such as the container 116, may be an absorbent dressing having an absorbent that is placed in the fluid path between a tissue site and a reduced-pressure source to receive fluid from the tissue site. In some embodiments, an absorbent dressing may place an absorbent adjacent a tissue site within a sealed therapeutic environment.

The absorbent 126 may function to hold, stabilize, and/or solidify fluids that may be collected from the tissue site 102. An absorbent may be of the type referred to as "hydrogels," "super-absorbents," or "hydrocolloids," for example. When disposed within the dressing 104, an absorbent may be formed into fibers or spheres to manifold reduced pressure until the absorbent 126 becomes saturated. Spaces or voids between the fibers or spheres may allow a reduced pressure that is supplied to the dressing 104 to be transferred within and through the absorbent 126 to the manifold 110 and the tissue site 102. The absorbent 126 may be a woven or non-woven material.

In some embodiments, an absorbent is formed of granular absorbent components that are scatter-coated onto a paper substrate. Scatter-coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate are passed through a calender machine to provide a smooth uniform surface to an absorbent.

In some exemplary embodiments, an absorbent may be formed of a superabsorbent polymer (SAP). Generally, relative to their mass, SAPs can absorb and retain large quantities of liquid, and in particular water. In some embodiments, SAPs may be formed from sodium polyacrylate. Sodium polyacrylate may be a sodium salt of polyacrylic acid. Sodium polyacrylate may be an anionic polyelectrolyte with negatively charged carboxylic groups in its main chain. SAPs may be formed in several ways, for example, by gel polymerization, solution polymerization, or suspension polymerization. Gel polymerization involves blending of acrylic acid, water, cross-linking agents, and UV initiator chemicals. The blended mixture is then placed into a reactor where the mixture is exposed to UV light to cause cross-linking reactions that form the SAP. The mixture may be dried and shredded before subsequent packaging and/or distribution. Solution polymerization involves a water based monomer solution that produces a mass of reactant polymerized gel. The monomer solution undergoes an exothermic reaction that drives the crosslinking of the monomers. Following the crosslinking process, the reactant polymer gel is chopped, dried, and ground to its final granule size. Suspension polymerization involves a water-based reactant suspended in a hydrocarbon-based solvent. However, the suspension polymerization process must be tightly controlled and is not often used.

High absorbing SAPs are based on ionic crosslinked hydrophilic polymers such as acrylics and acrylamides in the form of salts or free acids. SAPs absorb liquids by bonding with water molecules through hydrogen bonding. Hydrogen bonding involves the interaction of a polar hydrogen atom with an electronegative atom. As a result, SAPs absorb water based on the ability of the hydrogen atoms in each water molecule to bond with the hydrophilic polymers of the SAP having electronegative ionic components. Because the SAPs are ionic, they are affected by the soluble ionic components within the solution being absorbed and will, for example, absorb less saline than pure water, the sodium and chloride ions may block some of the water absorbing sites on the SAPs. For example, an SAP may absorb and retain de-ionized water up to 500 times the weight of the dry SAP. In volumetric terms, an SAP may absorb fluid volumes as high as 30 to 60 times the dry volume of the SAP. Other fluids having a higher ionic concentration may be absorbed at lower quantities.

In some exemplary embodiments, the absorbent 126 may have an area density of 800 grams per square meter (gsm), such as Texsus FP2325, for example. Area density may also be referred to as paper density and material density, for example. Area density may refer to a mass of a product per unit area of a type of fabric, paper, or paperboard. In some exemplary embodiments, the area density of the absorbent 126 may refer to the amount of SAP per square meter of a fiber substrate that forms the base of the absorbent 126. In some exemplary embodiments, the absorbent 126 may have an area density of 400 gsm, such as Texsus FP 2326, for example. In other exemplary embodiments, the absorbent 126 may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

The absorbent 126 may also have a free swell capacity. The free swell capacity may refer to the amount of deionized water that the SAP of the absorbent 126 may absorb per amount of the SAP and may be measured in grams/gram (g/g). In some embodiments, the absorbent 126 may have a free swell capacity of about 30 grams of water absorbed per gram of SAP, for example.

In some embodiments, the upstream layer 128 and the downstream layer 130 may have perimeter dimensions that are larger than the perimeter dimensions of the absorbent 126 so that the upstream layer 128 and the downstream layer 130 collectively surround the absorbent 126. For example, if the absorbent 126 is positioned between the upstream layer 128 and the downstream layer 130 and the center portions of the absorbent 126, the upstream layer 128 and the downstream layer 130 are aligned, the upstream layer 128 and the downstream layer 130 may extend beyond the perimeter of the absorbent 126. Peripheral portions of the upstream layer 128 and the downstream layer 130 may be coupled so that the upstream layer 128 and the downstream layer 130 enclose the absorbent 126. The upstream layer 128 and the downstream layer 130 may be coupled by high frequency welding, ultrasonic welding, heat welding, or impulse welding, for example. In other embodiments, the upstream layer 128 and the downstream layer 130 may be coupled by bonding or folding, for example.

The upstream layer 128 may be formed of non-woven material. A non-woven material may be a fabric-like material that includes long fibers that are bonded together. In some embodiments, the fibers may be bonded by one or more of chemical bonding, mechanical bonding, heat bonding, or solvent treatment bonding. Generally, small fibers are formed into a sheet or web and then bound with a mechanical process, such as with an adhesive, or in a thermal process where a binder is melted onto the web. In some embodiments, the upstream layer 128 may have a polyester fibrous porous structure. The upstream layer 128 may be porous, but preferably not perforated. In some embodiments, the upstream layer 128 may have an area density between about 80 gsm and about 150 gsm. In other embodiments, the area density may be lower or greater depending on the particular application of the container 116. In some embodiments, the upstream layer 128 may be formed of Libeltex TDL2, for example. In other embodiments, the upstream layer 128 may be formed of Libeltex TL4.

The downstream layer 130 may also be formed of a non-woven material. In some exemplary embodiments, the downstream layer 130 may have a polyester fibrous porous structure. The downstream layer 130 may be porous, but preferably not perforated. In some embodiments, the downstream layer 130 may have an area density between about 80 gsm and about 150 gsm. In other embodiments, the area density may be lower or greater depending on the particular application of the container 116. In some embodiments, the area density of the downstream layer 130 may be greater than the area density of the upstream layer 128. In other embodiments, the area density of the downstream layer 130 may be less than the area density of the upstream layer 128. In some embodiments, the upstream layer 128 and the downstream layer 130 may have a same area density. The downstream layer 130 may have a thickness greater than, less than, or equal to a thickness of the upstream layer 128. In some embodiments, the downstream layer 130 may be formed of Libeltex TL4. In other embodiments, the downstream layer 130 may be formed of Libeltex TDL2.

The upstream layer 128 and the downstream layer 130 contain the absorbent 126 and may reduce SAP loss during manufacturing, shipping, and use of the container 116. For example, if the container 116 is used at the tissue site 102, containment of the absorbent material may limit migration of the granular absorbent components into the tissue site 102. If the tissue site 102 is small, the container 116 may also aid the manifold 110 in the distribution of reduced pressure to the tissue site 102. The upstream layer 128 and the downstream layer 130 may also wick fluids from the tissue site 102 into the absorbent 126. The upstream layer 128 and the downstream layer 130 may prevent the loss of structural integrity associated with using scatter coated absorbent material to form the absorbent 126 that may often lead to more frequent replacement of the container 116.

Reduced pressure developed by the reduced-pressure source 106 may be delivered through the tube 112 to the connector 114. In some embodiments, the connector 114 may be a T.R.A.C.® Pad or Sensa T.R.A.C.® Pad available from Kinetic Concepts, Inc. (KCI) of San Antonio, Tex. The connector 114 may allow the reduced pressure to be delivered to the sealed therapeutic environment 124. In other embodiments, the connector 114 may also be a conduit inserted through the drape 108. The filter 132 may comprise a hydrophobic material substantially filling the fluid channel through the connector 114 and adapted to limit passage of liquids through the connector 114 into the tube 112.

The provision of reduced-pressure therapy with reduced-pressure therapy systems, such as the reduced-pressure therapy system 100, is increasingly being performed with smaller therapy devices that use battery power rather than a connection to an electrical outlet. Smaller therapy devices may also necessitate use of absorbent dressings to store fluid from the tissue site. Using an absorbent dressing rather than a separate fluid container may significantly decrease the amount of fluid that can be stored compared to a separate container. If the absorbent dressing is saturated, the reduced-pressure therapy must be stopped and the absorbent in the dressing replaced before reduced-pressure therapy may continue. Frequent removal and replacement of the dressing may cause irritation to a tissue site that could prolong healing times and cause pain to a patient. Frequent removal and replacement of the dressing may also increase the cost of providing reduced-pressure therapy.

In addition, an absorbent of an absorbent dressing may expand or swell as the absorbent absorbs fluid. If an absorbent is placed under a load, such as having a weight pressed against it or by being placed under a reduced pressure, the ability of the absorbent to expand may be decreased. If the ability of an absorbent to expand is decreased, the absorbent may absorb an amount of fluid that is less than a full fluid capacity of the absorbent. As a result, an absorbent dressing may need to be frequently removed and replaced to continue reduced-pressure therapy, which can increase healing times, pain, and costs. For example, an absorbent dressing, such as the dressing 104 may be coupled to the tissue site 102. The reduced-pressure source 106 may be fluidly coupled to the dressing 104 and operated to supply the sealed therapeutic environment 124 with a reduced pressure. If reduced pressure is supplied to the sealed therapeutic environment 124, a volume of the sealed therapeutic environment 124 may decrease, compressing the container 116 and the absorbent 126 between the manifold 110 and the drape 108. Compression of the container 116 and the absorbent 126 generally decreases the absorption capacity of the absorbent 126 as described above. To increase a fluid capacity of an absorbent dressing, and thereby decrease the frequency of dressing changes, the absorbent of the absorbent dressing can be increased in thickness. However, increasing the thickness of the absorbent may negatively affect the ability of a reduced-pressure source to provide reduced-pressure therapy.

As disclosed herein, the reduced-pressure therapy system 100 can overcome these challenges and others by increasing absorbent capacity through intermittent application of reduced pressure. In some embodiments, for example, the intermittent application of reduced pressure may include decreasing reduced pressure to manage fluid absorption. In yet more particular embodiments, a reduced-pressure source may provide reduced pressure that is allowed to decay periodically for a predetermined time period. In some embodiments, reduced pressure provided by a reduced-pressure source may be allowed to decay to an ambient pressure from the therapy pressure. Decay of reduced pressure or reduced-pressure decay may refer to the gradual decrease of reduced pressure in the sealed therapeutic environment 124 in the absence of a supply of reduced pressure. A decrease in reduced pressure in the sealed therapeutic environment 124 may occur as fluid from the tissue site 102 is drawn into the sealed therapeutic environment 124 by the supplied reduced pressure. A decrease in reduced pressure in the sealed therapeutic environment 124 may also occur due to gas permeating through the drape 108 into the sealed therapeutic environment 124 from the ambient environment. A decrease in reduced pressure in the sealed therapeutic environment 124 may also be caused by a leak between the drape 108 and the epidermis 118.

In some embodiments, the reduced-pressure source 106 may be fluidly coupled to an absorbent dressing, such as the dressing 104, having the absorbent 126. The reduced-pressure source 106 may control the expansion of the absorbent 126 by controlling the application of reduced pressure to the tissue site 102. In some embodiments, the reduced-pressure source 106 may reduce pressure in the sealed therapeutic environment 124 to the therapy pressure, compressing the absorbent 126. Once the therapy pressure is reached, the reduced-pressure source 106 may decrease the reduced pressure by allowing the reduced pressure in the sealed therapeutic environment 124 to decay. Decay of the reduced-pressure in the sealed therapeutic environment 124 may allow the absorbent 126 to expand. In some embodiments, if the pressure in the sealed therapeutic environment 124 reaches an ambient pressure, the reduced-pressure source 106 may be operated to supply reduced pressure until the pressure in the sealed therapeutic environment 124 reaches the therapy pressure. Each time the pressure in the sealed therapeutic environment 124 reaches the therapy pressure, the reduced pressure may be allowed to decay, and the cycle may be repeated periodically until the reduced-pressure therapy concludes. In other embodiments, the pressure in the sealed therapeutic environment 124 may be allowed to decay to a nominal reduced pressure. A nominal reduced pressure may be a reduced pressure that is greater than the ambient pressure but that is less than the therapy pressure. A nominal reduced pressure may be selected by an operator of the reduced-pressure therapy system 100.

Figure 2:
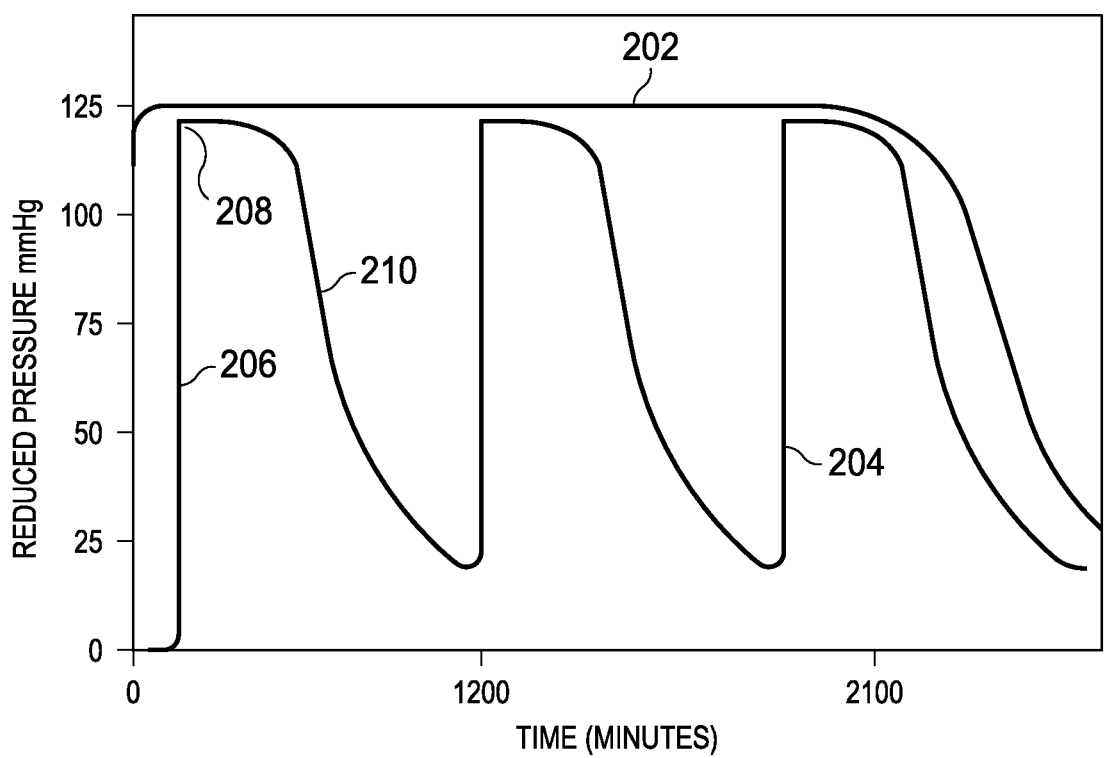
FIG. 2 is graph of a pressure profile in a sealed therapeutic environment provided by the system of FIG. 1.

FIG. 2 is a line chart of reduced pressure that is applied in a sealed therapeutic environment, illustrating details that may be associated with some embodiments. The vertical axis represents an amount of reduced pressure in mm Hg, and the horizontal axis represents an amount of time in minutes. FIG. 2 illustrates a pressure profile 202 of a pressure in a sealed therapeutic environment, such as the sealed therapeutic environment 124 during reduced-pressure therapy. As shown, the pressure profile 202 illustrates a substantially constant level of reduced-pressure. The pressure profile 202 may be maintained at about 125 mm Hg reduced pressure for the duration of reduced-pressure therapy. For example, the reduced-pressure source 106 may maintain a reduced pressure of about 125 mm Hg until the reduced-pressure source 106 is shut off at about 2100 minutes. After the reduced-pressure source 106 is shut off, the reduced pressure in the sealed therapeutic environment 124 may decay to ambient pressure.

FIG. 2 also illustrates another pressure profile 204 of the pressure in a sealed therapeutic environment. As shown by the pressure profile 204, the pressure in a sealed therapeutic environment may be reduced to about the therapy pressure. For example, the pressure profile 204 may have a draw-down 206 during which pressure is reduced to a therapy pressure 208. The pressure may be allowed to decay, as shown by a decay 210. For example, the pressure profile 204 may increase to about 125 mm Hg of reduced pressure while the reduced-pressure source 106 is operated, as shown during the draw-down 206. The reduced pressure may decrease during the decay 210 until about 1200 minutes when the pressure may again be reduced to about the therapy pressure. In some embodiments, the pressure profile 204 may decay to a nominal pressure that is about 25 mm Hg reduced pressure. In other embodiments, the pressure profile 204 may decay to an ambient pressure of about 0 mm Hg reduced pressure. The process may repeat until the conclusion of reduced-pressure therapy.

Referring again to FIG. 1, if the pressure is reduced in the sealed therapeutic environment 124, the drape 108 may compress the container 116 and the absorbent 126 against the manifold 110. For example, during the draw-down 206, the drape 108 may compress the container 116 against the manifold 110. As the reduced pressure decays during the decay 210, the amount of compression applied by the drape 108 may gradually decrease in proportion to the decrease in reduced pressure. The decreasing compression allows the absorbent 126 to expand. As the absorbent 126 expands, the absorbent 126 may distribute or redistribute fluid within a matrix of the absorbent 126. For example, the absorbent 126 may redistribute fluid into superabsorbent particles and between superabsorbent particles of the absorbent 126. Redistribution of fluid within the absorbent 126 may move fluid into areas not previously saturated and may allow saturated areas to become less saturated. If the reduced-pressure source 106 again supplies reduced pressure, the drape 108 may again compress the absorbent 126 against the manifold 110. The fluid previously absorbed by the absorbent 126 may prevent the absorbent 126 from being compressed as much as during the previous application of reduced pressure by the reduced-pressure source 106. If the therapy pressure is reached and the reduced-pressure source 106 stops supplying reduced pressure, allowing the reduced pressure in the sealed therapeutic environment 124 to decay, the absorbent 126 may again expand. Each compression and expansion of the absorbent 126 allows the absorbent 126 to increase its overall volume for fluid absorption while still providing reduced-pressure therapy.

In a working example, a first reduced-pressure source, such as the reduced-pressure source 106 was coupled to a first dressing, such as the dressing 104. The first reduced-pressure source was operated at a constant level of reduced pressure, about 125 mm Hg, for a therapy period, about 2400 minutes. The constant level of reduced pressure produced a pressure profile similar to the pressure profile 202. Fluid was supplied to the first dressing in periodic intervals. In the working example, an absorbent, such as the absorbent 126 having SAPs, absorbed approximately 50 cubic centimeters (cc) of fluid. A second reduced-pressure source, such as the reduced-pressure source 106, was fluidly coupled to a second dressing, such as the dressing 104, having an absorbent, such as the absorbent 126 having SAPs. The second reduced-pressure source was operated to reduce the pressure in sealed therapeutic environment formed by the second dressing to the therapy pressure, about 125 mm Hg. The reduced pressure was then allowed to decay to about 25 mm Hg before the second reduced-pressure source was operated to increase the reduced pressure to about 125 mm Hg. The cycle was repeated three times and produced a pressure profile similar to the pressure profile 204. By operating the second reduced-pressure source so that the reduced pressure in the sealed therapeutic environment decays, for example, as illustrated by the pressure profile 204, the second dressing experienced an increase of about 10% in the fluid storage capacity. For example, the second dressing subjected to the pressure profile 204 was able to absorb approximately 55 cc of fluid. By reapplying reduced pressure following the decay of the pressure in a sealed therapeutic environment, a tissue site may still experience the benefits of reduced pressure therapy while increasing a fluid absorption capacity to minimize the side effects of repeated dressing changes.

In some embodiments, the reduced-pressure source 106 may be operated in an intermittent mode of reduced-pressure therapy. An intermittent mode of reduced-pressure therapy may include a cyclic operation of the reduced-pressure source 106 so that the reduced-pressure source 106 increases reduced pressure for a periodic interval of time and decreases reduced pressure for period intervals of time, such as in the pressure profile 204. Operating the reduced-pressure source 106 in the intermittent mode may further increase the fluid absorption capacity of the absorbent 126. For example, the reduced-pressure source 106 may operate to provide reduced pressure for intervals of one minute and stop providing reduced pressure for intervals of two minutes, decreasing the reduced pressure. For example, during the intermittent mode, the reduced-pressure source 106 may compress the absorbent 126 for one minute during the application of reduced pressure and expand the absorbent 126 for two minutes during a period of decay.

Figure 3:
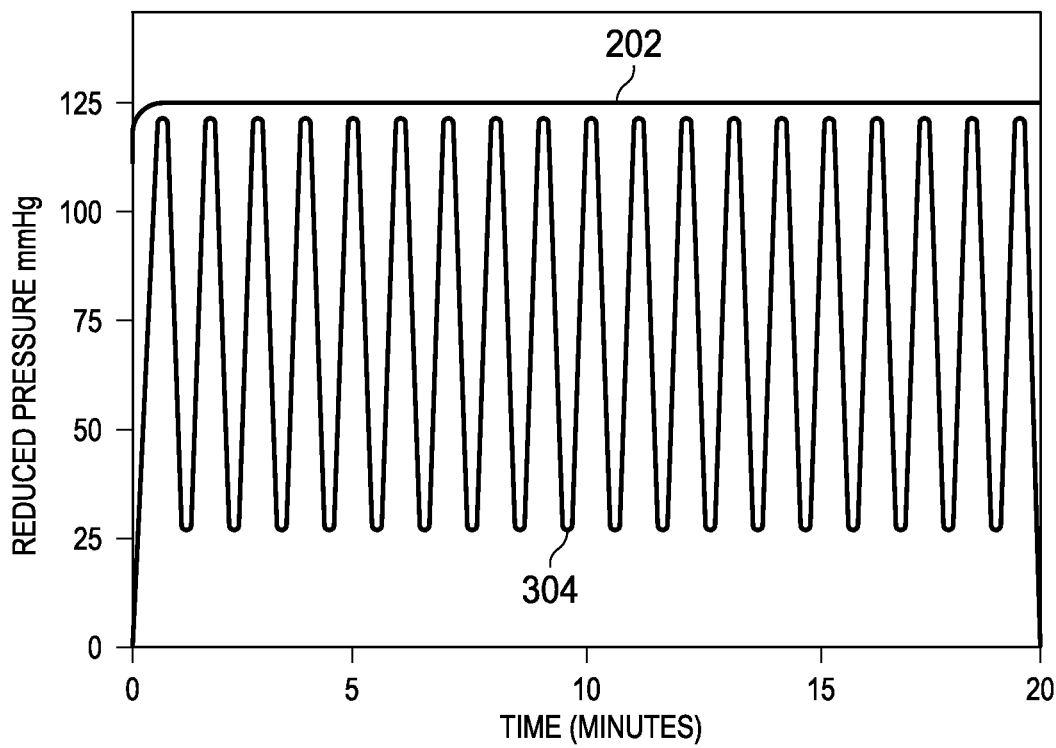
FIG. 3 is graph of another pressure profile in a sealed therapeutic environment provided by the system of FIG. 1.

FIG. 3 is a line chart of reduced pressure that may be applied in the sealed therapeutic environment 124, illustrating details that may be associated with some embodiments. The vertical axis represents an amount of reduced pressure in mm Hg, and the horizontal axis represents an amount of time in minutes. The pressure profile 202 of FIG. 2 is provided for reference. The reduced-pressure source 106 may be operated in an intermittent mode so that reduced pressure is supplied for one minute and the reduced-pressure source 106 is turned off for one minute, a 1/1 intermittent mode. The 1/1 intermittent mode may produce a pressure profile 304 in the sealed therapeutic environment 124. In the example embodiment of FIG. 3, if the reduced-pressure source 106 is operating, the reduced pressure may increase to about 125 mm Hg. If the reduced-pressure source 106 is not operating, the reduced pressure may decay to about 25 mm Hg. During the one minute that the reduced-pressure source 106 operates, the drape 108 may compress the container 116 against the manifold 110, and during the one minute that the reduced-pressure source 106 is not operating, the absorbent 126 of the container 116 may expand as the reduced pressure decays. In some embodiments, the reduced-pressure source 106 may be operated to decrease the reduced pressure or increase the decay rate by permitting ambient pressure to flow through the reduced-pressure source 106 to the sealed therapeutic environment 124.

Figure 4:
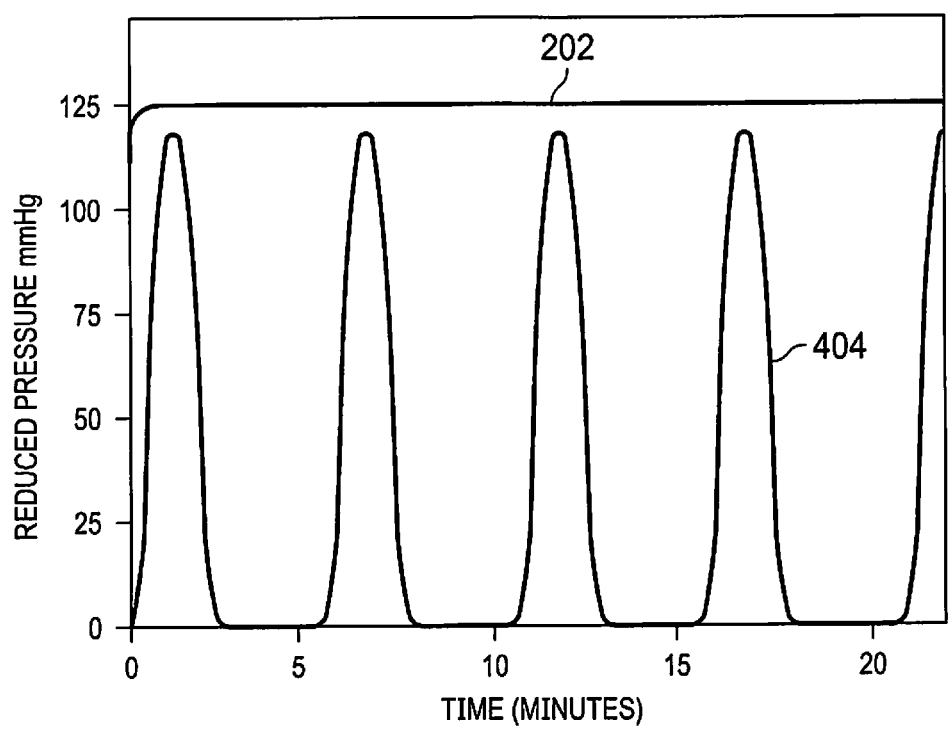
FIG. 4 is graph of another pressure profile in a sealed therapeutic environment provided by the system of FIG. 1.

FIG. 4 is a line chart of reduced pressure that may be applied in the sealed therapeutic environment 124, illustrating details that may be associated with some embodiments. The vertical axis represents an amount of reduced pressure in mm Hg, and the horizontal axis represents an amount of time in minutes. The pressure profile 202 of FIG. 2 is also provided in FIG. 4 for reference. For example, a pressure profile 404 can be provided if the reduced-pressure source 106 is operated in an intermittent mode so that reduced pressure is supplied for one minute and the reduced-pressure source 106 is turned off for five minutes, a 1/5 intermittent mode. In the example of FIG. 4, the pressure profile 404 illustrates an increase in the reduced pressure in the sealed therapeutic environment to about 125 mm Hg reduced pressure and a decrease in the reduced pressure to about 0 mm Hg reduced pressure. In some embodiments the sealed therapeutic environment 124 may remain at about 0 mm Hg until the end of the five minute period. During the one minute intervals that the reduced-pressure source 106 operates, the drape 108 may compress the container 116 against the manifold 110, and during the five minute intervals that the reduced-pressure source 106 is not operating, the absorbent 126 of the container 116 may expand. In some embodiments, once the pressure in the sealed therapeutic environment 124 reaches 0 mm Hg, the absorbent 126 may swell as more fluid is absorbed. In some embodiments, the reduced-pressure source 106 may be operated to increase the decay rate by permitting ambient pressure to flow through the reduced-pressure source 106 to the sealed therapeutic environment 124.

In a working example using the 1/1 and the 1/5 intermittent modes, a first dressing, similar to the dressing 104 having the absorbent 126 formed of SAPs, was fluidly coupled to a first reduced-pressure source, similar to the reduced-pressure source 106, and provided a constant level of reduced pressure. In the working example, the reduced pressure in a sealed therapeutic environment formed by the first dressing was maintained at about 125 mm Hg for the duration of the reduced-pressure therapy. A second dressing, similar to the dressing 104 having the absorbent 126 formed from SAPs, was coupled to a second reduced-pressure source, similar to the reduced-pressure source 106, and operated in an intermittent mode. The second dressing experienced an increase of fluid absorption between about 15% and about 36% in the intermittent mode of reduced-pressure therapy when compared to the constant application of reduced pressure. For example, the 1/1 intermittent mode with a dressing positioned in a vertical position increased in fluid storage capacity by about 15%. The 1/1 intermittent mode with a dressing positioned in an inverted position increased in fluid storage capacity by about 36%. When the therapy interval increased to 1 minute of reduced pressure and 5 minutes of no reduced pressure, the storage capacity increased further in both the vertical and inverted dressing positions.

Figure 5:
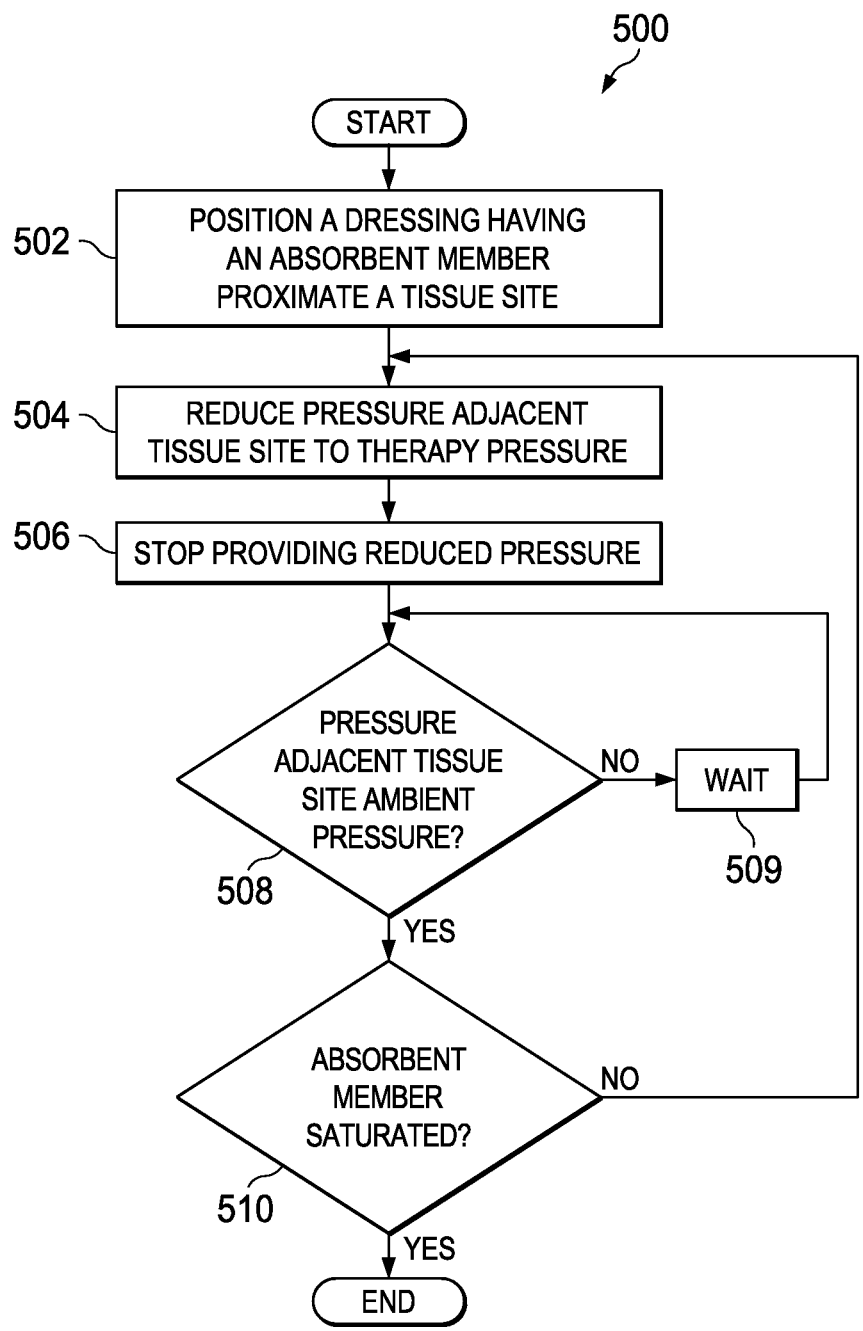
FIG. 5 is a flow chart depicting logical operational steps of a method for providing reduced-pressure therapy in accordance with some embodiments.

FIG. 5 illustrates a flow chart 500 of logical operations that can be implement in some embodiments of the reduced-pressure therapy system 100 of FIG. 1 during reduced-pressure therapy. For example, the operations may be implemented by a controller, such as the controller 107, configured to execute the operations. At block 502, a dressing having an absorbent may be positioned proximate a tissue site. For example, the dressing 104 having the absorbent 126 may be positioned adjacent the tissue site 102 to form the sealed therapeutic environment 124. At block 504, a reduced-pressure source may reduce pressure adjacent the tissue site to a therapy pressure. For example, the reduced-pressure source 106 may provide reduced pressure to the sealed therapeutic environment 124 until a pressure in the sealed therapeutic environment 124 is about the therapy pressure. At block 506, the reduced-pressure source may stop providing reduced pressure. For example, the reduced-pressure source 106 may stop providing reduced pressure to the sealed therapeutic environment 124. At block 508, the system can determine if the pressure adjacent the tissue site is about an ambient pressure. For example, a pressure sensor in the reduced-pressure source 106 may determine if the pressure in the sealed therapeutic environment 124 is about an ambient pressure. If the pressure adjacent the tissue site is not about the ambient pressure at block 508 (NO), the system can wait for a predetermined time period at block 509 and continue at block 508, where the system can determine if the pressure adjacent the tissue site is about an ambient pressure. If the pressure adjacent the tissue site is about the ambient pressure at block 508 (YES), the system can continue to block 510. At block 510, the system can determine if the absorbent is saturated. For example, a moisture sensor of the reduced-pressure source 106 may determine if absorbent 126 is saturated. If the absorbent is not saturated at block 510 (NO), the system can continue at block 504 where reduced pressure is provided until the pressure in the sealed therapeutic environment is about the therapy pressure. If the absorbent is saturated at block 510 (YES), the system can stop.

Figure 6:
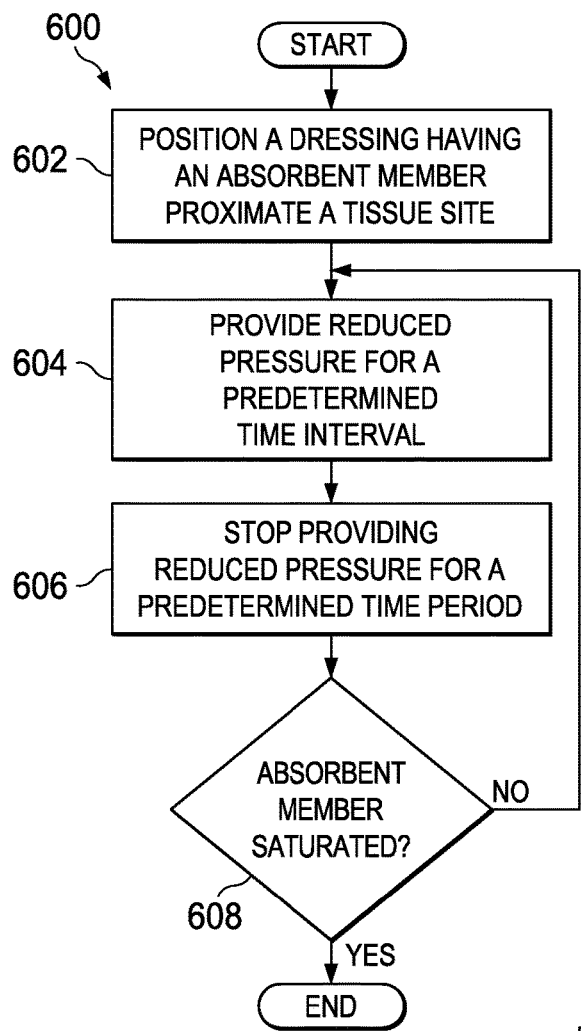
FIG. 6 is a flow chart depicting logical operational steps of another method for providing reduced-pressure therapy in accordance with some embodiments.

FIG. 6 illustrates a flow chart 600 of logical operations that can be implemented in some embodiments of the reduced-pressure therapy system 100 of FIG. 1 during reduced-pressure therapy. For example, the operations may be implement by a controller, such as the controller 107, configured to execute the operations. At block 602, a dressing having an absorbent may be positioned proximate a tissue site. For example, the dressing 104 having the absorbent 126 may be positioned adjacent the tissue site 102 to form the sealed therapeutic environment 124. At block 604, a reduced-pressure source may provide reduced pressure for a predetermined time period. For example, the reduced-pressure source 106 may provide reduced pressure to the sealed therapeutic environment 124 for a predetermined time interval. In some embodiments, the predetermined time interval may be between about 1 minute and about 20 minutes. At block 606, the reduced-pressure source may stop providing reduced pressure for a predetermined time period. For example, the reduced-pressure source 106 may stop providing reduced pressure to the sealed therapeutic environment 124 for a predetermined time interval. In some embodiments, the predetermined time interval of no reduced pressure may be between about 1 minute and about 20 minutes. At block 608, the system can determine if the absorbent is saturated. If the absorbent is not saturated at block 608 (NO), the system can continue at block 604 where reduced pressure is provided for the predetermined interval. If the absorbent is saturated at block 608 (YES), the system can stop.

Figure 7:
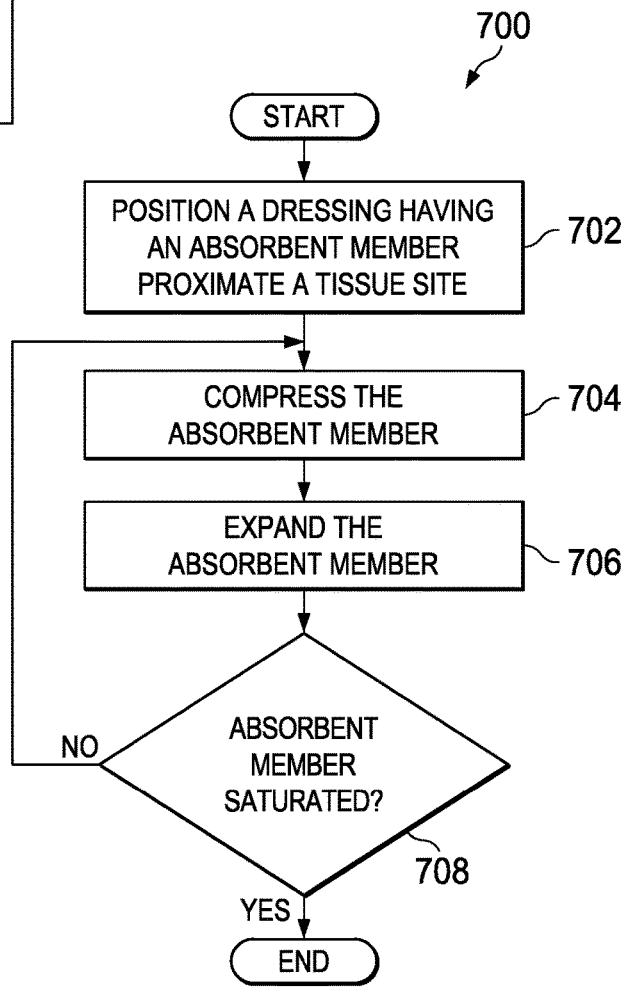
FIG. 7 is a flow chart depicting logical operational steps of another method for providing reduced-pressure therapy in accordance with some embodiments.

FIG. 7 illustrates a flow chart 700 of logical operations that can be implemented in some embodiments of the reduced-pressure therapy system 100 of FIG. 1 during reduced-pressure therapy. For example, the operations may be implement by a controller, such as the controller 107, configured to execute the operations. At block 702, a dressing having an absorbent may be positioned proximate a tissue site. For example, the dressing 104 having the absorbent 126 may be positioned adjacent the tissue site 102 to form the sealed therapeutic environment 124. At block 704, a reduced-pressure source may compress the superabsorbent. For example, the reduced-pressure source 106 may provide reduced pressure to the sealed therapeutic environment 124, compressing the absorbent 126. At block 706, the reduced-pressure source may expand the absorbent 126. For example, the reduced-pressure source 106 may provide no reduced pressure to the sealed therapeutic environment 124, permitting the absorbent 126 to expand as the reduced pressure in the sealed therapeutic environment 124 decays. At block 708, the system can determine if the absorbent is saturated. If the absorbent is not saturated at block 708 (NO), the system can continue at block 704 where the absorbent is compressed. If the absorbent is saturated at block 708 (YES), the system can stop.

The systems and methods described herein may provide significant advantages, some of which have already been mentioned. For example, the reduced-pressure system may provide a dressing having an increased fluid absorption capacity without requiring an increase in a thickness of the absorbent. Furthermore, the reduced-pressure system may increase the fluid absorption capacity of the absorbent while continuing to provide reduced-pressure therapy.

Although the certain features, aspects, operations, and their advantages have been disclosed in the context of certain illustrative, non-limiting embodiments, it should be understood that various changes, substitutions, permutations, and alterations can be made without departing from the scope of the invention as defined by the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A method for managing liquid absorption from a tissue site, the method comprising:
    positioning an absorbent pouch proximate the tissue site, the absorbent pouch comprising:
        a first outer layer comprising a non-woven material;
        a second outer later comprising a non-woven material; and
        an absorbent enclosed by the first outer layer and the second outer layer, the absorbent comprising a matrix of superabsorbent polymer particles and configured to receive and retain liquid from the tissue site, and the absorbent being dry;
    sealing a sealing member to tissue proximate the tissue site to form a therapeutic environment containing the absorbent pouch;
    fluidly coupling a reduced-pressure source to the therapeutic environment by a conduit and a connector;
    positioning a filter between the absorbent pouch and the conduit, the filter comprising a hydrophobic material and configured to limit liquid flow from the therapeutic environment into the conduit;
    periodically supplying reduced pressure to the therapeutic environment with the reduced-pressure source for one minute;
    decaying the reduced pressure in the therapeutic environment for periodic intervals of one minute by periodically stopping the supply of the reduced pressure from the reduced-pressure source; and
    in response to decaying the reduced pressure in the therapeutic environment, expanding the absorbent, wherein expansion of the absorbent redistributes the liquid from the tissue site into and between the superabsorbent polymer particles of the absorbent, and increasing a liquid storage capacity of the absorbent between about 15% and about 36%.

2. The method of claim 1, wherein periodically supplying reduced pressure comprises periodically supplying reduced pressure until a pressure in the therapeutic environment is a therapy pressure.

3. The method of claim 1, wherein decaying the reduced pressure in the therapeutic environment comprises delivering ambient air to the therapeutic environment.

4. A system for providing reduced pressure to a tissue site, the system comprising:
- a reduced-pressure source;
- a container configured to be positioned between the tissue site and the reduced-pressure source, the container comprising:
  - an upstream layer formed from a non-woven material,
  - a downstream layer formed from a non-woven material, and
  - an absorbent formed from a matrix of superabsorbent polymer particles disposed between the upstream layer and the downstream layer, the absorbent having a free swell capacity of about 30 grams of water absorbed per gram of superabsorbent polymer, and the absorbent configured to receive and retain liquid from the tissue site;
- a sealing member configured to be sealed over the container to form a therapeutic environment;
- a conduit configured to fluidly couple the reduced-pressure source and the therapeutic environment;
- a filter configured to be disposed between the container and the conduit, the filter comprising a hydrophobic material and configured to limit liquid flow from the therapeutic environment into the conduit; and
- a controller configured to operate the reduced-pressure source to periodically supply reduced pressure to the therapeutic environment to compress the absorbent and to periodically stop the supply of the reduced pressure to allow a pressure in the therapeutic environment to decay for periodic intervals of a predetermined time period and to expand the absorbent, wherein an expansion of the absorbent redistributes the liquid from the tissue site into and between the superabsorbent polymer particles of the absorbent, and increase a liquid storage capacity of the absorbent between about 15% and about 36%.

5. The system of claim 4, wherein the absorbent is a granular superabsorbent polymer.

6. The system of claim 4, wherein the superabsorbent polymer comprises sodium polyacrylate.

7. The system of claim 4, wherein the controller is configured to operate the reduced-pressure source to periodically supply reduced pressure for one minute.

8. The system of claim 4, wherein the predetermined time period is between about 1 minute and about 20 minutes.

9. The system of claim 4, wherein the predetermined time period is about five minutes.

10. The system of claim 4, wherein the controller is configured to operate the reduced-pressure source to reduce a pressure in the therapeutic environment to a therapy pressure.

11. The system of claim 4, wherein the controller is configured to operate the reduced-pressure source to deliver ambient pressure to the therapeutic environment.

12. The system of claim 4, wherein peripheral portions of the downstream layer are coupled to the upstream layer to enclose the absorbent.

13. The system of claim 4, wherein the absorbent has an area density of 400 grams per square meter.

14. The system of claim 4, wherein the absorbent has an area density of 800 grams per square meter.

15. The system of claim 4, wherein the absorbent comprises spheres configured to allow reduced pressure to be transferred within and through the absorbent.

* * * * *

UNITED STATES PATENT AND TRADEMARK OFFICE
CERTIFICATE OF CORRECTION

PATENT NO. : 10,610,623 B2
APPLICATION NO. : 14/619743
DATED : April 7, 2020
INVENTOR(S) : Robinson et al.

It is certified that error appears in the above-identified patent and that said Letters Patent is hereby corrected as shown below:

On the Title Page

Page 3, Column 2, item [56]
Line 33, delete "F.E. E" and insert -- F.E. --, therefor.
Line 45, delete "Hypermia" and insert -- Hyperemia --, therefor.

In the Specification

Column 8
Lines 51-52, delete "capralactones." and insert -- caprolactones. --, therefor.
Line 61, delete "hydroxy apatites," and insert -- hydroxyapatites, --, therefor.

Column 9
Line 67, delete "water-based" and insert -- water based --, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*